(12) United States Patent
Fischvogt

(10) Patent No.: US 8,696,557 B2
(45) Date of Patent: Apr. 15, 2014

(54) ACCESS ASSEMBLY INCLUDING INFLATABLE SEAL MEMBER

(75) Inventor: Greg Fischvogt, Hamden, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 13/223,613

(22) Filed: Sep. 1, 2011

(65) Prior Publication Data

US 2012/0157779 A1  Jun. 21, 2012

Related U.S. Application Data

(60) Provisional application No. 61/425,331, filed on Dec. 21, 2010.

(51) Int. Cl.
*A61B 17/02* (2006.01)
(52) U.S. Cl.
USPC .......................................... 600/207; 600/208
(58) Field of Classification Search
USPC .................................. 600/201–246
See application file for complete search history.

(56) References Cited

U.S. PATENT DOCUMENTS

| | | | |
|---|---|---|---|
| 3,402,710 A | 9/1968 | Paleschuck | |
| 3,777,757 A | 12/1973 | Gray et al. | |
| 4,112,932 A | 9/1978 | Chiulli | |
| 4,984,564 A | 1/1991 | Yeun | |
| 5,269,772 A | 12/1993 | Wilk | |
| 5,342,385 A | 8/1994 | Norelli et al. | |
| 5,361,752 A * | 11/1994 | Moll et al. | 600/205 |
| 5,395,367 A | 3/1995 | Wilk | |
| 5,480,410 A | 1/1996 | Cuschieri et al. | |
| 5,490,843 A | 2/1996 | Hildwein et al. | |
| 5,507,758 A | 4/1996 | Thomason et al. | |
| 5,511,564 A | 4/1996 | Wilk | |
| 5,514,133 A | 5/1996 | Golub et al. | |
| 5,524,644 A | 6/1996 | Crook | |
| 5,545,150 A | 8/1996 | Danks et al. | |
| 5,634,911 A | 6/1997 | Hermann et al. | |
| 5,634,937 A | 6/1997 | Millenauer et al. | |
| 5,803,921 A | 9/1998 | Bonadio | |

(Continued)

FOREIGN PATENT DOCUMENTS

| | | |
|---|---|---|
| EP | 1 312 318 | 5/2003 |
| EP | 2 044 889 | 4/2009 |

(Continued)

OTHER PUBLICATIONS

European Search Report for corresponding EP11194532 date of mailing is Mar. 8, 2012 (8 pgs).

(Continued)

*Primary Examiner* — Jerry Cumberledge

(57) ABSTRACT

An access assembly for insertion through an opening in tissue is provided. The access assembly includes a flexible outer sleeve having an upper rim formed on a proximal end, a lower rim formed on a distal end and defining a longitudinal opening extending therebetween. The lower rim may define an inflatable space that in a deflated state facilitates insertion of the lower rim through tissue and in an inflated state assists in retaining the access assembly in place relative to the tissue. The access assembly further includes an inflatable member secured within the longitudinal opening of the outer sleeve. The inflatable member includes a plurality of inflatable lobes configured to selectively receive at least one surgical device therebetween in a sealing manner.

18 Claims, 5 Drawing Sheets

(56) References Cited

U.S. PATENT DOCUMENTS

| | | | |
|---|---|---|---|
| 5,830,191 A | 11/1998 | Hildwein et al. | |
| 5,833,603 A | 11/1998 | Kovacs et al. | |
| 5,911,757 A | 6/1999 | Seare, Jr. | |
| 5,997,515 A * | 12/1999 | de la Torre et al. | 604/256 |
| 6,004,303 A | 12/1999 | Peterson | |
| 6,033,426 A | 3/2000 | Kaji | |
| 6,033,428 A | 3/2000 | Sardella | |
| 6,440,063 B1 | 8/2002 | Beane et al. | |
| 6,486,588 B2 | 11/2002 | Doron et al. | |
| 6,551,270 B1 | 4/2003 | Bimbo et al. | |
| 6,578,577 B2 | 6/2003 | Bonadio et al. | |
| 6,723,088 B2 | 4/2004 | Gaskill, III et al. | |
| 6,846,287 B2 * | 1/2005 | Bonadio et al. | 600/208 |
| 6,908,430 B2 * | 6/2005 | Caldwell et al. | 600/207 |
| 6,939,296 B2 * | 9/2005 | Ewers et al. | 600/206 |
| 7,008,377 B2 | 3/2006 | Beane et al. | |
| 7,052,454 B2 | 5/2006 | Taylor | |
| 7,125,382 B2 | 10/2006 | Zhou et al. | |
| 7,297,112 B2 | 11/2007 | Zhou et al. | |
| 7,416,530 B2 | 8/2008 | Turner et al. | |
| 7,481,765 B2 * | 1/2009 | Ewers et al. | 600/208 |
| 7,563,250 B2 | 7/2009 | Wenchell | |
| 7,657,297 B2 | 2/2010 | Simpson et al. | |
| 7,686,762 B1 | 3/2010 | Najafi et al. | |
| 7,850,600 B1 * | 12/2010 | Piskun | 600/114 |
| 2002/0019635 A1 | 2/2002 | Wenstrom | |
| 2003/0014076 A1 * | 1/2003 | Mollenauer et al. | 606/213 |
| 2004/0092795 A1 * | 5/2004 | Bonadio et al. | 600/207 |
| 2004/0236192 A1 | 11/2004 | Necola Shehada et al. | |
| 2005/0004478 A1 | 1/2005 | Fitz | |
| 2005/0096695 A1 | 5/2005 | Olich | |
| 2005/0165317 A1 | 7/2005 | Turner et al. | |
| 2006/0020241 A1 | 1/2006 | Piskun et al. | |
| 2006/0149306 A1 | 7/2006 | Hart et al. | |
| 2006/0161049 A1 * | 7/2006 | Beane et al. | 600/207 |
| 2006/0161050 A1 * | 7/2006 | Butler et al. | 600/208 |
| 2006/0200012 A1 | 9/2006 | Mansour et al. | |
| 2006/0200220 A1 | 9/2006 | Brown et al. | |
| 2006/0247500 A1 * | 11/2006 | Voegele et al. | 600/208 |
| 2007/0027371 A1 | 2/2007 | Benaron et al. | |
| 2007/0060884 A1 | 3/2007 | Hayek | |
| 2007/0085232 A1 * | 4/2007 | Brustad et al. | 264/102 |
| 2008/0027476 A1 | 1/2008 | Piskun | |
| 2008/0033273 A1 | 2/2008 | Zhou et al. | |
| 2008/0058652 A1 | 3/2008 | Payne | |
| 2008/0058728 A1 | 3/2008 | Soltz et al. | |
| 2008/0108885 A1 | 5/2008 | Colvin, Jr. | |
| 2008/0154101 A1 | 6/2008 | Jain et al. | |
| 2008/0161826 A1 | 7/2008 | Guiraudon | |
| 2008/0255519 A1 | 10/2008 | Piskun et al. | |
| 2008/0287788 A1 | 11/2008 | Richardson et al. | |
| 2009/0054908 A1 | 2/2009 | Zand et al. | |
| 2009/0093752 A1 | 4/2009 | Richard et al. | |
| 2009/0093850 A1 | 4/2009 | Richard | |
| 2009/0118587 A1 * | 5/2009 | Voegele et al. | 600/206 |
| 2009/0163782 A1 | 6/2009 | Shehada et al. | |
| 2009/0209969 A1 | 8/2009 | Wolfe | |
| 2009/0221966 A1 | 9/2009 | Richard | |
| 2009/0299153 A1 | 12/2009 | Gerber et al. | |
| 2010/0081895 A1 | 4/2010 | Zand | |
| 2010/0100043 A1 | 4/2010 | Racenet | |
| 2010/0240960 A1 | 9/2010 | Richard | |
| 2010/0249523 A1 | 9/2010 | Spiegal et al. | |
| 2010/0249524 A1 | 9/2010 | Ransden et al. | |
| 2010/0286484 A1 | 11/2010 | Stellon et al. | |
| 2010/0298646 A1 | 11/2010 | Stellon et al. | |
| 2010/0312065 A1 * | 12/2010 | Shelton et al. | 600/207 |
| 2011/0028891 A1 | 2/2011 | Okoniewski | |
| 2011/0034778 A1 | 2/2011 | Kleyman | |
| 2011/0054257 A1 | 3/2011 | Stopek | |
| 2011/0054258 A1 | 3/2011 | O'Keefe et al. | |
| 2011/0082341 A1 | 4/2011 | Kleyman et al. | |
| 2011/0082343 A1 | 4/2011 | Okoniewski | |
| 2011/0082346 A1 | 4/2011 | Stopek | |
| 2011/0124967 A1 * | 5/2011 | Morgan et al. | 600/204 |
| 2011/0125186 A1 | 5/2011 | Fowler et al. | |
| 2011/0166423 A1 | 7/2011 | Farascioni et al. | |
| 2012/0130179 A1 * | 5/2012 | Rockrohr | 600/205 |
| 2012/0190932 A1 * | 7/2012 | Okoniewski | 600/207 |

FOREIGN PATENT DOCUMENTS

| | | |
|---|---|---|
| EP | 2 095 781 | 9/2009 |
| EP | 2 098 182 | 9/2009 |
| EP | 2 229 900 | 9/2010 |
| EP | 2 238 924 | 10/2010 |
| EP | 2 238 925 | 10/2010 |
| EP | 2 248 478 | 11/2010 |
| EP | 2 253 283 | 11/2010 |
| EP | 2 272 450 | 1/2011 |
| EP | 2 289 438 | 3/2011 |
| EP | 2 292 165 | 3/2011 |
| WO | WO 93/14801 | 8/1993 |
| WO | WO99/29250 A1 | 6/1999 |
| WO | WO 00/54675 | 9/2000 |
| WO | WO00/54675 A1 | 9/2000 |
| WO | WO 2008/121294 | 10/2008 |
| WO | WO2010/141673 A1 | 12/2010 |

OTHER PUBLICATIONS

European Search Report from EP Application No. EP 12152164 dated Apr. 19, 2012.

European Search Report from EP Application No. EP 12152128 dated Apr. 20, 2012.

* cited by examiner

ACCESS ASSEMBLY INCLUDING INFLATABLE SEAL MEMBER

CROSS REFERENCE TO RELATED APPLICATION

The present application claims the benefit of and priority to U.S. Provisional Application Ser. No. 61/425,331 filed on Dec. 21, 2010, the entire contents of which are incorporated herein by reference.

BACKGROUND

1. Technical Field

The present disclosure relates to access assemblies for use in surgical procedures. More particularly, the present disclosure relates to access assemblies including an inflatable seal member.

2. Background of Related Art

Access assemblies configured for reception through an incision into an abdominal cavity are known, as are methods of inserting the access assemblies therethrough. Traditional access assemblies include a rigid cannula that is received through the tissue of the body wall into the body cavity. Endoscopic, laparoscopic and other suitable instruments may then be directed through a housing on the proximal end of the cannula to access the body cavity in a sealing manner through the access assembly.

Compressible assemblies configured for accessing a body cavity and permitting reception of instruments therethrough in sealing manner are also known. Such compressible assemblies are composed of silicone, thermoplastic elastomers (TPE), rubber, foam, gel and other compressible materials and are configured to be compressed to facilitate insertion into an incision. Typically, such assemblies are deformed by a surgeon using his/her fingers or with the assistance of a grasping device, e.g., forceps. Compression of the assembly reduces the profile of the assembly, thereby facilitating reception of the assembly into the incision. Upon release of the compressive force, the compressed assembly returns to an uncompressed configuration. In the uncompressed configuration, the access assembly seals the incision into the body cavity. The assembly may have one or more sealed passageways for receiving instruments therethrough and may optionally be configured for connection with a source of insufflation gas.

Compression of the compressible assemblies may cause damage to the assembly during insertion, thereby reducing or eliminating the effectiveness of the assembly. Expansion of the compressible assembly from a compressed configuration to an uncompressed configuration once received in an incision may cause tissue damage if the assembly is not properly sized. Alternatively, the assembly may not decompress sufficiently to create a seal.

Therefore, it is desirable to provide an access assembly including an inflatable seal member.

SUMMARY

An access assembly for insertion through an opening in tissue is provided. The access assembly includes a flexible outer sleeve having an upper rim formed on a proximal end, a lower rim formed on a distal end and defining a longitudinal opening extending therebetween. The lower rim may define an inflatable space that in a deflated state facilitates insertion of the lower rim through tissue and in an inflated state assists in retaining the access assembly in place relative to the tissue.

The access assembly further includes an inflatable member secured within the longitudinal opening of the outer sleeve. The inflatable member includes a plurality of inflatable lobes configured to selectively receive at least one surgical device therebetween in a sealing manner. The upper rim may be configured to be selectively inflated. At least one of the upper and lower rims may be configured to be compressed. The upper rim may have a diameter greater than a diameter of the central portion.

In an embodiment, the access assembly may include one, two, three or more inflatable lobes. The outer sleeve may be integrally formed with the inflatable member. Complete deflation of the plurality of inflatable lobes may cause inward collapse of at least one of upper and lower rims. Each of the plurality of inflatable lobes may be operably connected to a source of inflation fluid. Each of the plurality of inflatable lobes may be independently connected to a source of inflation fluid. At least one of the inflatable lobes may be wedge-shaped. The plurality of inflatable lobes may be coated with a material to provide at least one of preventing the lobes from sticking together, facilitating a seal between the lobes and facilitating reception of a surgical device therethrough. The inflatable member may be configured to simultaneously receive two or more surgical devices therethrough.

DESCRIPTION OF THE DRAWINGS

Embodiments of a flexible access assembly are disclosed herein with reference to the drawings, wherein.

DETAILED DESCRIPTION

Embodiments of the presently disclosed access assembly will now be described in detail with reference to the drawings wherein like numerals designate identical or corresponding elements in each of the several views. As is common in the art, the term "proximal" refers to that part or component closer to the user or operator, e.g. surgeon or physician, while the term "distal" refers to that part or component further away from the user. Although the access assemblies of the present disclosure will be described as relates to accessing an abdominal cavity through an incision in the abdominal wall, the access assemblies of the present disclosure may be modified for use in other closed procedures, e.g., laparoscopic, arthroscopic, endoscopic. Furthermore, the access assemblies of the present disclosure may be modified for use in accessing internal cavities through natural orifices, e.g., anus, vagina.

Figure 1:
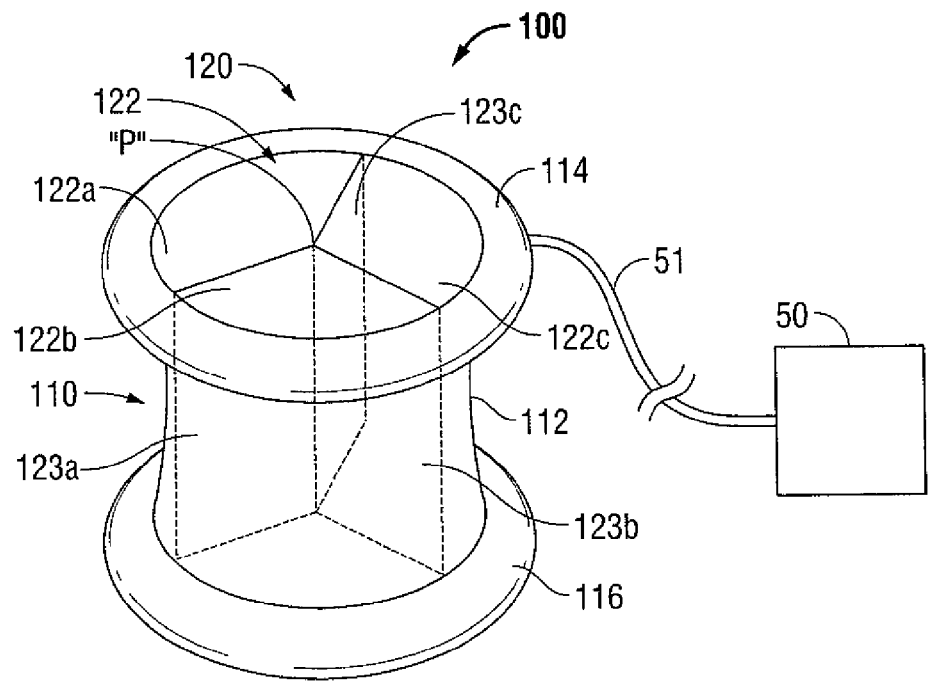
FIG. 1 is a perspective view of an embodiment of an access assembly according to the present disclosure.

Referring initially to FIG. 1, an access assembly according to an embodiment of the present disclosure is shown generally as access assembly 100. Access assembly 100 is selectively inflatable to allow for insertion of access assembly 100 through an opening in the body of a patient such that after insertion and inflation, access assembly 100 creates a seal within the incision through which a surgeon may insert and manipulate one or more surgical instruments to complete a procedure.

Figure 6:
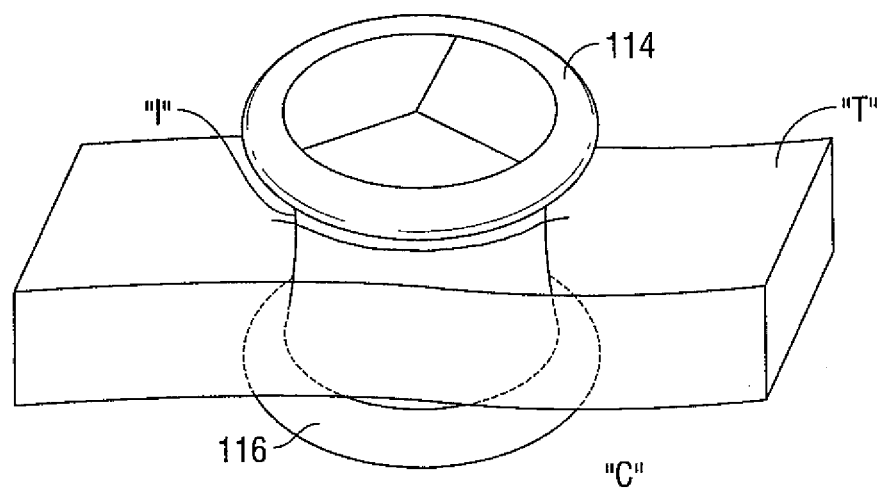
FIG. 6 is a perspective view of the flexible access assembly of FIG. 1 positioned through the incision in the tissue.

With reference to FIGS. 1-4, access assembly 100 includes a flexible outer sleeve 110 and an inflatable seal member 120. Outer sleeve 110 defines a substantially annular body 112 having an upper rim 114 located at a proximal end thereof and a lower rim 116 located at a distal end thereof. Body 112 of sleeve 110 defines a longitudinal opening 113 therethrough configured to receive inflatable seal member 120 therein. Annular body 112 is configured to span the thickness of tissue "T" (FIG. 6). Upper and lower rims 114, 116 aid in preventing movement of access assembly 100 longitudinally through incision "I" (FIG. 6). As the thickness of tissue "T" depends on the body composition of the patient and the location through which the underlying cavity is being accessed, the length and size of access assembly 100 may be modified to suit a given procedure.

Still referring to FIGS. 1-4, outer sleeve 110 of access assembly 100 may be formed of various materials such as, for example, silicone, thermoplastic elastomers (TPE), rubber, foam, gel, etc. In one embodiment, annular body 112 includes TPE material that is infused with an inert gas, e.g. $CO_2$ or Nitrogen, to form a foam structure. Body 112 may be coated with a lubricant, e.g. Parylene N or C, in order to create a lubricious surface. Various other coatings, e.g., hydrophilic, hydrophobic, bio-agents, anti-infection, analgesic, may also be employed to improve the access assembly or to adapt access assembly 100 for a specific procedure. Upper and lower rims 114, 116 of sleeve 110 may be formed of the same or different material as body 112. Upper and lower rims 114, 116 may be integrally formed with body 112, or may instead be securely affixed thereto by adhesive, welding, bonding or any other suitable method. As shown, each of upper and lower rims 114, 116 define an inflatable space or cavity 114a, 116a, respectively. Although not shown, it is envisioned that annular body 112 may also define a cavity (not show) configured for selective inflation to assist in securing access assembly 100 with incision "I".

Figure 4:
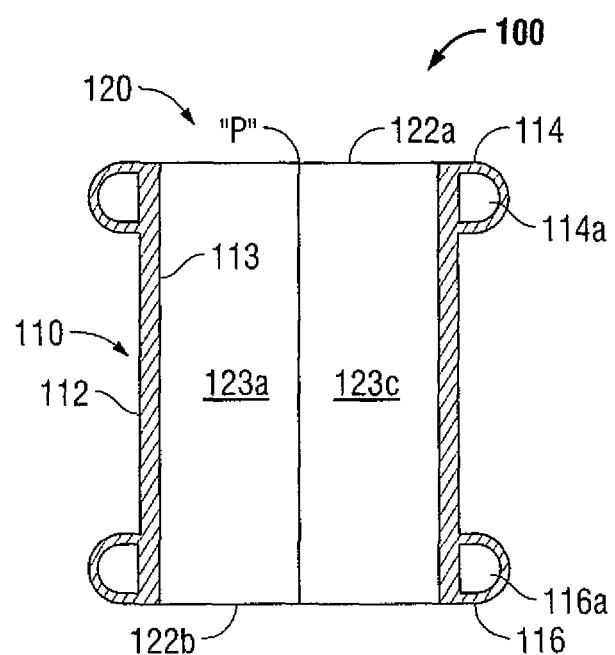
FIG. 4 is a cross-sectional side view of the access assembly of FIG. 3.

With particular reference now to FIG. 4, cavities 114a, 116a of upper and lower rims 114, 116 are operably connected to a source of inflation fluid 50 (FIG. 1) by an inflation tube 51 to selectively inflate upper and lower rims 114, 116. Each of upper and lower rims 114, 116 may be serially coupled with source of inflation fluid 50 such that both rims 114, 116 inflate simultaneously. Alternatively, each of upper and lower rims 114, 116 are independently coupled to source of inflation fluid 50 such that rims 114, 116 may be inflated independently. In this manner, accidental or intentional deflation of one of rims 114, 116 does not cause the deflation of the other of rims 114, 116. This may be accomplished using separate inflation ports or through the use of a valve assembly (not shown). Since upper rim 114 is never received within incision "I", and therefore, does not require deflation, it is envisioned that upper rim 114 may be provided to a clinician fully inflated. Cavities 114a, 116a may be inflated using any suitable fluid, including but not limited to air and water. Source of inflation fluid 50 may include a hand pump, a disposable gas cartridge, an air compressor, water faucet or any other suitable means. Alternatively, upper and lower rims 114, 116 are self-inflating. In this manner, cavities 114a, 116a of upper and lower rims 114, 116 are provided with negative pressure or suction. Upon opening of a valve assembly (not shown), ambient air is drawn into each of cavities 114a, 116a, thereby causing inflation of upper and lower rims 114, 116. In another embodiment, upper and lower rims 114, 116 are not inflatable, but instead are composed of a compressible material that permits compression of rims 114, 116, thereby facilitating insertion of access assembly 100 into incision "I".

Still referring to FIGS. 1-4, inflatable seal member 120 is securely received within longitudinal cavity 113 formed in annular body 112 of sleeve 110. Inflatable seal member 120 includes a plurality of inflatable lobes 122. As shown, inflatable seal member 120 includes three (3) inflatable lobes 122a, 122b, 122c. Alternatively, inflatable seal member 120 may include two (FIG. 9) or more (FIG. 10) inflatable lobes. Inflatable lobes 122 extend the length of longitudinal opening 113 and define wedge-shaped members. As shown, each of inflatable lobes 122a, 122b, 122c are substantially similar. It is envisioned that one or more of lobes 122a, 122b, 122c may have a different configuration. For example, one of lobes 122a, 122b, 122c may not extend the entire length of longitudinal opening 113. Alternatively, one of lobes 122a, 122h, 122c may have a proximal or distal flange extending outwardly therefrom to further ensure inflatable member 120 creates a seal. Inflatable lobes 122a, 122b, 122c are configured to engage at least one other of lobes 122a, 122b, 122c along an entire length of longitudinal opening 113 in sleeve 110. Alternatively, each of lobes 122a, 122b, 122c is configured to engage the other of lobes 122a, 122b, 122c along only a portion of opening 113. Longitudinal slots 123a, 123b, 123c are formed between inflatable lobes 122a, 122b, 122c to enable sealed passage of one or more surgical devices "D1", "D2" (FIG. 8) through longitudinal opening 113 of annular body 112.

Any or all of inflatable lobes 122a, 122b, 122c may be secured to the other of inflatable lobes 122a, 122b, 122c at a point common to two or more of lobes 122a, 122b, 122c. As shown, inflatable lobes 122a, 122b, 122c are secured to one another at a point "P" at a proximal end of inflatable seal member 120. In an alternative embodiment, one or more of lobes 122a, 122b, 122c may be secured to the other of lobes 122a, 122b, 122c at a distal end of inflatable seal member 120, and/or any point between the proximal and distal ends of inflatable member 120. Securing lobes 122a, 122b, 122c to one another at one or more locations ensures contact between lobes 122a, 122b, 122c, thereby ensuring a seal is maintained through inflatable member 120. Lobes 122a, 122b, 122c may be secured to the other of lobes 122a, 122b, 122c using adhesive, welding, bonding, mechanical fasteners or any other suitable means. Lobes 122a, 122b, 122c may further include a lining (not shown) on external surfaces thereof to protect lobes 122a, 122b, 122c from tearing or being punctured as one or more surgical devices "D1", "D2" (FIG. 7) are inserted therethrough.

With reference still to FIGS. 1-4, as discussed above, inflatable lobes 122 are configured such that one or more surgical devices "D1", "D2" may be inserted through one or more of longitudinal slots 123a, 123b, 123c in a sealed manner. Inflatable lobes 122 may be coated with one or more lubricious substances (not shown) to facilitate insertion of surgical devices "D1", "D2" therethrough. Alternatively, or in addition, inflatable lobes 122 may be coated with one or more substances to assist in creating a seal between each of lobes 122a, 122b, 122c. Further, inflatable lobes 122 may be provided with a coating for preventing sticking of lobes 122a, 122c, 122c to one another.

Figure 2:
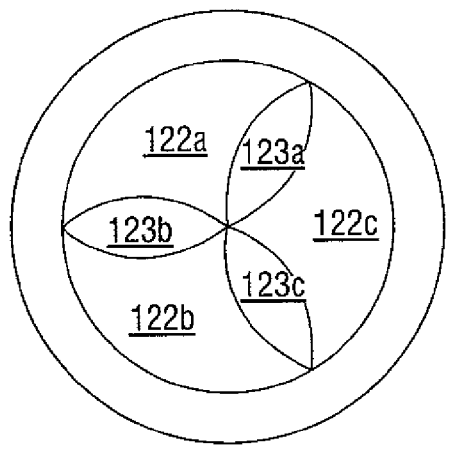
FIG. 2 is a top view of the access assembly of FIG. 1, including an inflatable seal member in a partially deflated condition.

With particular reference now to FIG. 2, inflatable member 120 of access assembly 100 is shown with lobes 122a, 122b, 122c in a semi-deflated condition. In the semi-deflated condition, the space created between lobes 122a, 122b, 122c allows access assembly 100 to be compressed to facilitate insertion of access assembly 100 though incision "I" (FIG. 6). It is further envisioned that inflatable member 120 may be further deflated by providing inflatable member 120 with suction to further deflate lobes 122a, 122b, 122c. Further deflation of lobes 122a, 122b, 122c may cause inward collapse of upper and lower rims 114, 116, thereby reducing the profile of access assembly 100 and facilitating insertion of access assembly 100 through incision "I". Access assembly 100 may be provided to a surgeon in either the deflated or semi-deflated conditions.

Figure 3:
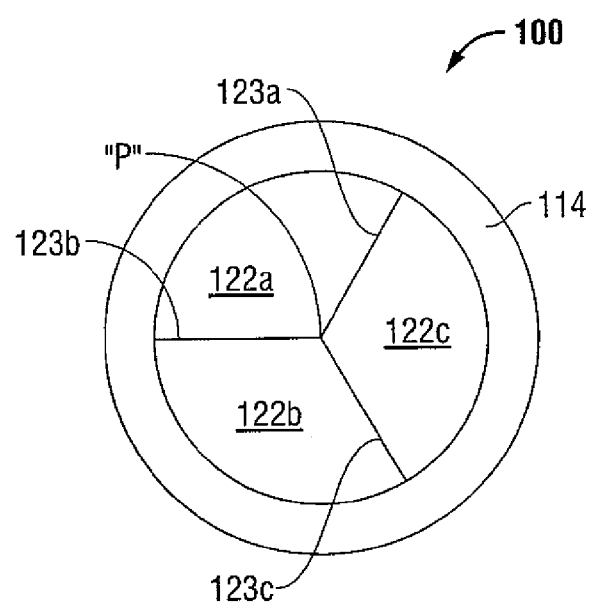
FIG. 3 is a top view of the access assembly of FIGS. 1 and 2, including the inflatable seal member in an inflated condition.

With particular reference now to FIG. 3, inflatable member 120 of access assembly 100 is shown with lobes 122a, 122b, 122c in a fully inflated condition. Access assembly 100 may be provided to a surgeon in the fully inflated condition, or as discussed above, in the deflated or semi-deflated configuration. Inflatable member 120 is operably connected to source of inflation fluid 50. Alternatively, inflatable member 120 may be configured to self-inflate. As shown, the inflation fluid source is the same as that used to inflate upper and lower rims 114, 116. Alternatively, inflatable member 120 may be inflated by an independent or separate source of inflation fluid (not shown). Lobes 122a, 122b, 122c may be inflated individually or simultaneously. Lobes 122a, 122b, 122c may be partially inflated or partially deflated to permit passage of one or more large devices "D3" (FIG. 10) therethrough. It is envisioned that inflatable member 120 may be configured such that upon accidental deflation of one or more of lobes 122a, 122b, 122c, the other of lobes 122a, 122b, 122c may be additional inflated to compensate for the loss of the deflated lobe.

The use of access assembly 100 will now be described with reference to FIGS. 5A-8. The following discussion will include using access assembly 100 for accessing a body cavity "C" through an incision "I". As discussed above, access assembly 100 may be used for accessing other cavities or lumen through other openings in the body, including naturally occurring orifices, e.g., anus. Initially, incision "I" is created in tissue "T" using conventional methods, e.g., scalpel, tissue punch, to provide access to body cavity "C".

Figure 5A:
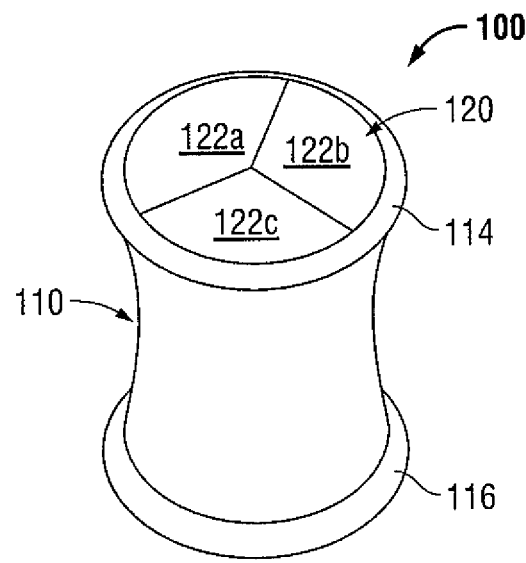
FIG. 5A is a perspective view of the access assembly of FIGS. 1-4, including inflatable upper and lower rims in a deflated condition.
Figure 5B:
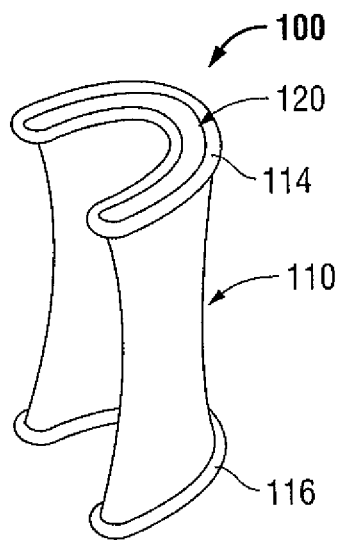
FIG. 5B is a perspective view of the access assembly of FIG. 1, including the inflatable seal member in a completely deflated condition.

Referring initially to FIG. 5A, in one embodiment, at least lower rim 116 of sleeve 110 is deflated to facilitate insertion of access assembly through incision "I". Turning to FIG. 5B, as discussed above, inflatable member 120 may also, or instead, be completely deflated or semi-deflated to facilitate insertion of access assembly 100 through incision "I". Once at least semi-deflated, access assembly 100 may be compressed to facilitate insertion through incision "I". Complete deflation of lobes 122a, 122b, 122c of inflatable member 120 may cause upper and lower rims 114, 116 to collapse radially inwardly, thereby further facilitating insertion of access assembly 100 through incision "I". Alternatively, and as discussed above, upper and lower rims 114, 116 of sleeve 110 may instead be formed of a compressible material that permits a user to compress rims 114, 116 to facilitate insertion access assembly 100 through incision "I".

Turning briefly to FIG. 6, once received through incision "I", either or both of upper and lower rims 114, 116 and inflatable member 120 are inflated to secure access assembly 100 within incision "I" and thereby seal body cavity "C". As discussed above, upper and lower rims 114, 116 may be inflated independently or simultaneously. Lobes 122a, 122b, 122c may also be inflated independently or simultaneously.

Figure 7:
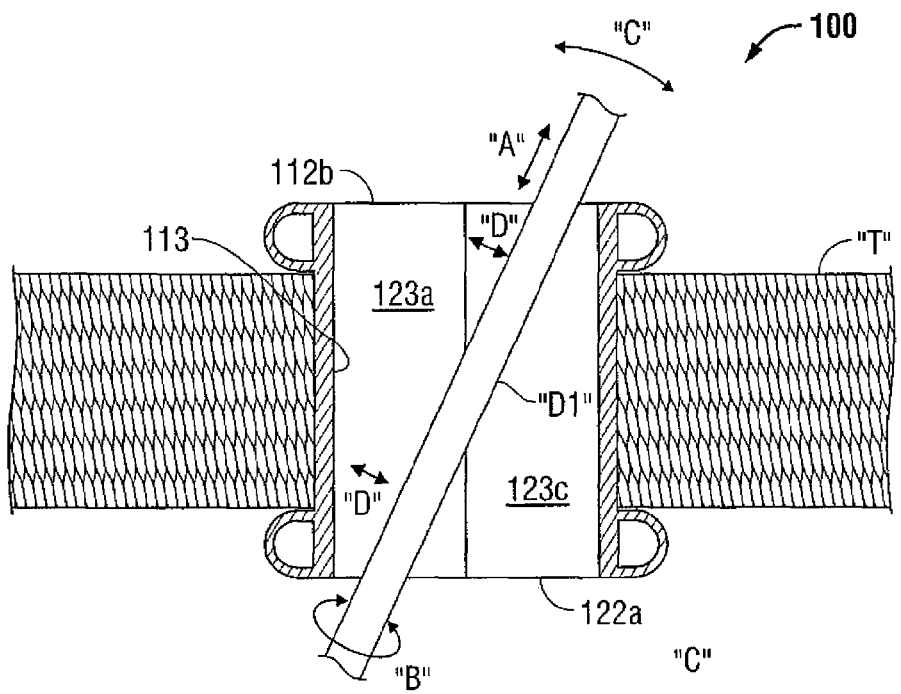
FIG. 7 is a side view, partially shown in cross-section, of the access assembly of FIG. 1, including a surgical device received therethrough.
Figure 8:
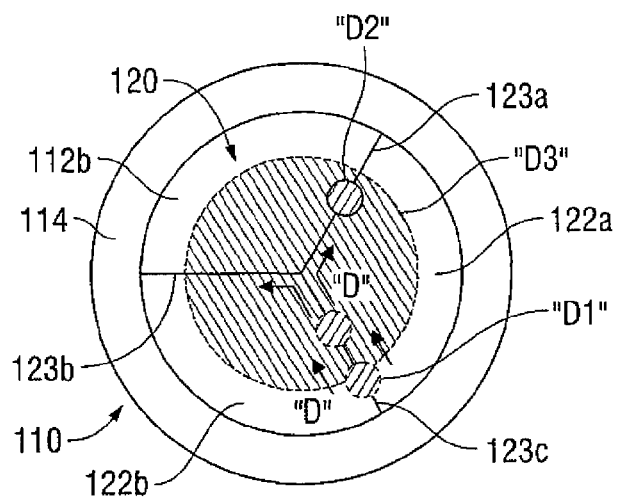
FIG. 8 is a top view of the access assembly of FIG. 1, including multiple surgical devices inserted therethrough.

With reference now to FIG. 8, access assembly 100 may be operated in a traditional manner. As discussed above, each longitudinal slots 123a, 123b, 123c are configured to receive one or more surgical devices "D1", "D2" therethrough. As shown in FIG. 7, a surgical device "D1" received through any of longitudinal slots 123a, 123b, 123c may be withdrawn and retracted through inflatable member 120, as indicated by arrows "A", rotated about a longitudinal axis thereof, as indicated by arrows "B", pivoted about an axis, as indicated by arrow "C" and/or be laterally translated within longitudinal opening 113, as indicated by arrows "D" while inflatable member 120 maintains a seal thereabout. One or more surgical devices "D1", "D2" may be manipulated in this manner. As discussed above, any or all of lobes 122a, 122b, 122c may be partially deflated to permit reception of a surgical device "D3" having an increased diameter. Once removed, any or all of lobes 122a, 122b, 122c may be re-inflated to seal longitudinal opening 113.

Removal of access assembly 100 from within incision "I" occurs in the reverse order of insertion. Either or both of inflatable sleeve 110 and inflatable member 120 are at least partially deflated to facilitate removal of access assembly 100 from incision "I". Access assembly 100 may further be compressed to facilitate withdrawal from incision "I". Once access assembly 100 is removed from incision "I", incision "I" is closed in a conventional manner.

Figure 9:
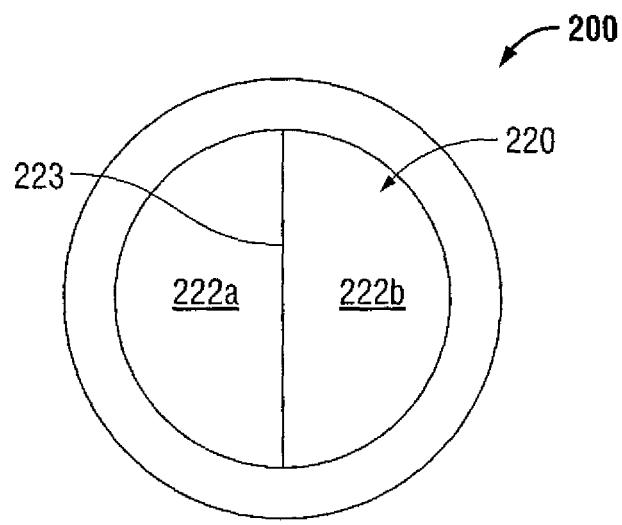
FIG. 9 is a top view of an access assembly according to an alternative embodiment of the present disclosure.
Figure 10:
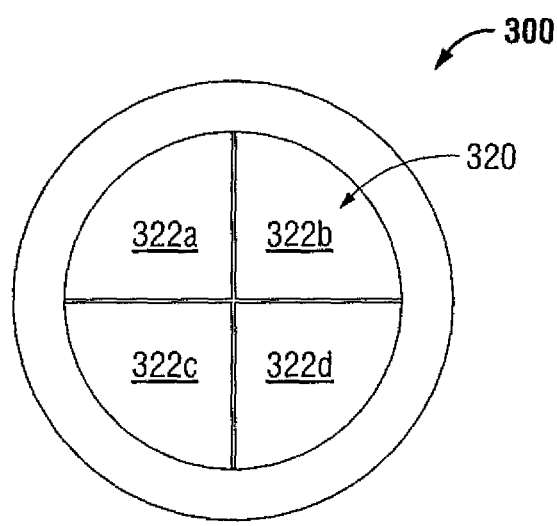
FIG. 10 is a top view of an access assembly according to another embodiment of the present disclosure.

Turning briefly to FIGS. 9 and 10, alternative embodiments of access assemblies according to the present disclosure are shown generally as access assemblies 200, 300. Access assembly 200, 300 are substantially similar to access assembly 100 described hereinabove, and will only be described as relates to the differences therebetween. Referring initially to FIG. 9, access assembly 200 includes an inflatable member 220 having first and second inflatable lobes 222a, 222b. Inflatable lobes 222a, 222b define a longitudinal slot 223 therebetween configured to receive one or more surgical devices "D1", "D2", "D3" (FIG. 8). Turning to FIG. 10, in another embodiment, access assembly 300 includes an inflatable member 320 having four (4) inflatable lobes 322a, 322b, 322c, 322d.

It will be understood that various modifications may be made to the embodiments disclosed herein. For example, as noted hereinabove, the disclosed access assembly may be provided with multiple inflatable lobes in excess of the disclosed four lobes. Additionally, the size and configuration of the disclosed inflatable lobes not be identical but may be varied depending upon the contemplated surgical device to be utilized therethrough. Therefore, the above description should not be construed as limiting, but merely as exemplifications of particular embodiments. Those skilled in the art will envision other modifications within the scope and spirit of the claims appended hereto.

The invention claimed is:
1. An access assembly for insertion through tissue, the access assembly comprising:
 a flexible outer sleeve having an upper rim formed on a proximal end, a lower rim formed on a distal end and defining a longitudinal opening extending therebetween; and an inflatable member secured within the longitudinal opening of the outer sleeve, the inflatable member including at least three inflatable lobes secured to one another at a common point prior to inflation of the inflatable lobes, adjacent lobes having sidewalls and defining a shared longitudinal slot configured to selectively receive at least one surgical device in a sealing manner, the adjacent lobes being expandable toward each other such that the sidewalls are engageable with one another.

2. The access assembly of claim 1, wherein at least one of the upper and lower rims is configured to be selectively inflated.

3. The access assembly of claim 1, wherein at least one of the upper and lower rims is configured to be compressed.

4. The access assembly of claim 1, wherein the upper rim has a diameter greater than a diameter of a central portion of the flexible outer sleeve.

5. The access assembly of claim 1, wherein the flexible outer sleeve is integrally formed with the inflatable member.

6. The access assembly of claim 1, wherein complete deflation of any of the inflatable lobes causes inward collapse of at least one of the upper and lower rims.

7. The access assembly of claim 1, wherein each of the inflatable lobes is operably connected to a source of inflation fluid.

8. The access assembly of claim 1, wherein each of the inflatable lobes is independently connected to a source of inflation fluid.

9. The access assembly of claim 1, wherein at least one of the inflatable lobes is wedge-shaped.

10. The access assembly of claim 1, wherein the inflatable lobes are coated with a material to provide at least one of the following: to prevent the inflatable lobes from sticking together, to facilitate a seal between the inflatable lobes or to facilitate reception of a surgical device therethrough.

11. The access assembly of claim 1, wherein the inflatable member is configured to simultaneously receive two or more surgical devices therethrough.

12. The access assembly of claim 1, wherein the longitudinal slot is substantially linear and is configured to enable lateral translation of a surgical device within the longitudinal slot.

13. An access assembly for insertion through tissue, the access assembly comprising:
    a flexible outer sleeve defining a longitudinal opening extending therethrough; and
    an inflatable member secured within the longitudinal opening of the outer sleeve, the inflatable member including at least three inflatable lobes secured to one another at a common point prior to inflation of the inflatable lobes, and a plurality of longitudinal slots defined by sidewalls of adjacent inflatable lobes configured to receive at least one surgical device, the inflatable lobes and the longitudinal slots sharing a common point of intersection, the inflatable lobes being expandable toward each other such that the sidewalls are engageable with one another.

14. The access assembly of claim 13, wherein the longitudinal slots extend radially outward from the common point of intersection.

15. The access assembly of claim 13, wherein the inflatable lobes are repositionable between an uninflated condition, wherein the longitudinal slots define an opening extending therethrough, and an inflated condition, wherein the longitudinal slots are sealed.

16. An access assembly for insertion through tissue, the access assembly comprising:
    a flexible outer sleeve defining a longitudinal opening extending therethrough; and
    an inflatable member secured within the longitudinal opening of the outer sleeve, the inflatable member including at least three inflatable lobes to one another at a common point prior to inflation of the inflatable lobes and longitudinal slots defined by sidewalls of adjacent inflatable lobes, wherein adjacent inflatable lobes share a common longitudinal slot and adjacent inflatable lobes are expandable toward each other such that the sidewalls are engageable with one another when expanded.

17. The access assembly of claim 16, wherein the inflatable lobes are repositionable between an uninflated condition, wherein the longitudinal slots define an opening extending therethrough, and an inflated condition, wherein the longitudinal slots are sealed.

18. The access assembly of claim 16, wherein the longitudinal slots define outer boundaries of the inflatable lobes.

* * * * *